United States Patent
Miao et al.

(10) Patent No.: US 11,359,073 B2
(45) Date of Patent: Jun. 14, 2022

(54) SELF-REINFORCED STARCH-BASED MULTIFUNCTIONAL MATERIALS AND PROCESSING METHOD THEREOF

(71) Applicant: Jiangnan University, Wuxi (CN)

(72) Inventors: Ming Miao, Wuxi (CN); Xue Jia, Wuxi (CN); Osvaldo H. Campanella, Wuxi (CN); Zhengyu Jin, Wuxi (CN); Tao Zhang, Wuxi (CN); Lei Ye, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 17/524,801

(22) Filed: Nov. 12, 2021

(65) Prior Publication Data

US 2022/0073706 A1 Mar. 10, 2022

(30) Foreign Application Priority Data

Dec. 9, 2020 (CN) .......................... 202011450446.6

(51) Int. Cl.
| | |
|---|---|
| *A61K 47/36* | (2006.01) |
| *B65D 65/46* | (2006.01) |
| *C08B 31/00* | (2006.01) |
| *C08B 31/04* | (2006.01) |
| *C08B 31/10* | (2006.01) |
| *C08L 3/08* | (2006.01) |
| *C08J 5/18* | (2006.01) |
| *C08L 3/06* | (2006.01) |

(52) U.S. Cl.
CPC ................ *C08L 3/08* (2013.01); *A61K 47/36* (2013.01); *B65D 65/466* (2013.01); *C08B 31/006* (2013.01); *C08B 31/04* (2013.01); *C08B 31/10* (2013.01); *C08J 5/18* (2013.01); *C08L 3/06* (2013.01); *C08J 2303/06* (2013.01); *C08J 2303/08* (2013.01); *C08L 2203/02* (2013.01); *C08L 2203/16* (2013.01); *C08L 2205/025* (2013.01); *C08L 2312/00* (2013.01)

(58) Field of Classification Search
CPC .... C08L 3/08; C08L 2203/02; C08L 2203/16; C08L 2205/025; C08L 2312/00; A61K 47/36; B65D 65/466; C08B 31/006; C08B 31/04; C08B 31/01; C08B 31/00; C08J 5/18; C08J 2303/06; C08J 2303/08; C08K 3/06
See application file for complete search history.

(56) References Cited

U.S. PATENT DOCUMENTS 5,439,953 A 8/1995 Ritter et al.

FOREIGN PATENT DOCUMENTS

| CN | 107214929 A | 9/2017 |
|---|---|---|
| CN | 108102148 A | 6/2018 |

*Primary Examiner* — Alma Pipic
(74) *Attorney, Agent, or Firm* — IPro, PLLC

(57) ABSTRACT

Disclosed is a processing method of a self-reinforced starch-based multifunctional material, and belongs to the technical field of starch deep processing. The processing method takes bulk starch as a base material, including the following steps: firstly reacting starch nanoparticles with an organic acid anhydride reagent and adding a bacteriostatic agent to prepare composite nanoparticles, then mixing the composite nanoparticles with the bulk starch, an etherifying agent, a crosslinking agent, a plasticizer and the like, and finally preparing a starch-based multifunctional material by dry extrusion modification combined with a starch-based nanoparticle assembly and reinforcement technology. The method of the disclosure is simple and convenient in step, mild and controllable in reaction, and continuous and green in production. The obtained product has good mechanical properties, high barrier properties and high antibacterial properties, can be applied to many fields such as food, textiles, daily chemicals and medicine, and has a broad market prospect.

7 Claims, 1 Drawing Sheet

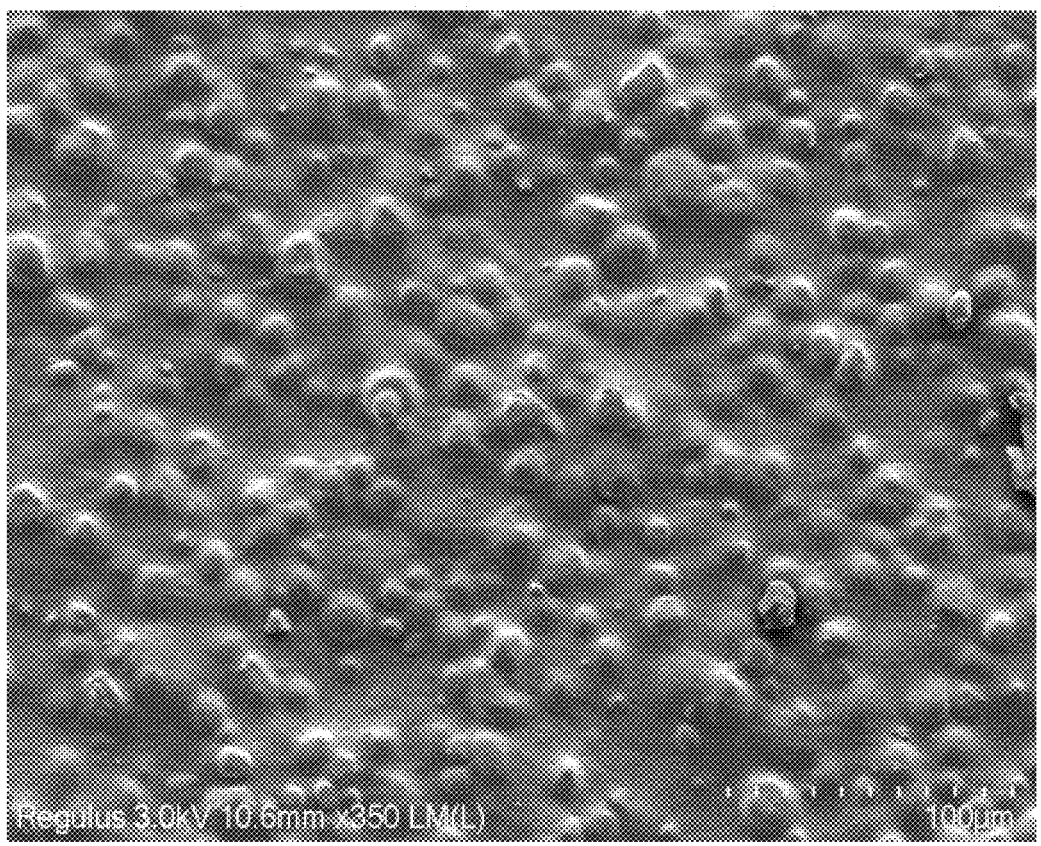

SELF-REINFORCED STARCH-BASED MULTIFUNCTIONAL MATERIALS AND PROCESSING METHOD THEREOF

TECHNICAL FIELD

The disclosure relates to a processing method of a self-reinforced starch-based multifunctional material, and belongs to the field of starch deep processing.

BACKGROUND

The large-scale use of plastic products, while facilitating human life, also brings a big problem-"white pollution". At present, most of the plastics on the market are produced by petrochemical products. More than 75% of plastics are petroleum-based plastics, and about 20% of recycled plastics are basically made from petroleum-based plastics. Petroleum-based plastics, like PVC, PP, and PE, have good physical and chemical properties, but because the garbage produced after use cannot be degraded, petroleum-based plastics exist in the natural environment for a long time and are the main source of white pollution. To reduce the pollution of natural resources and reduce the dependence on increasingly depleted resources, research and development of degradable polymer materials derived from renewable resources have become a focus of attention.

As an international strategic emerging industry, biodegradable materials made from natural renewable starch as raw materials have received extensive attention from developed countries and are showing a momentum of rapid development. In China, bulk starch resources are sufficient. In 2019, the output of starch exceeded 32 million tons, most of which are used to manufacture starch sugar, fermented products and other industrial raw materials. Compared with developed countries in Europe and America, China's starch deep processing level is not high, and the product quality is low and there are fewer varieties. At the same time, the development and utilization of starch-based materials in China are still in their infancy. Compared with the international advanced level, China still has gaps in product performance, manufacturing costs, key technologies, industrialization scale, etc. For example, Japan, the United States, and Italy all have companies claiming that they have successfully developed all-starch thermoplastics and have formed large-scale production and sales. Most of the degradable starch plastic products produced by enterprises in China are of a filling type, and only the added starch can be degraded, while general-purpose resin can only be pyrolyzed in the environment, is difficult to recycle and will affect the soil health. Based on the above reasons, to overcome the natural defects of starch-based materials such as poor mechanical properties and poor water resistance, there is an urgent need to develop a processing method of a self-reinforced starch-based multifunctional material.

SUMMARY

To solve the above problems, the disclosure provides a processing method of a self-reinforced starch-based multifunctional material, and the self-reinforced starch-based multifunctional material of the disclosure has excellent mechanical properties, barrier properties and antibacterial properties, and can be used as packaging materials in the fields of food, textiles, daily chemicals, medicine and the like. The method of the disclosure has the characteristics of simple technology, controllable process, environmental protection and the like.

The first objective of the disclosure is to provide a processing method of a self-reinforced starch-based multifunctional material, including the following steps:

(1) mixing starch nanoparticles and an organic acid anhydride reagent in an aqueous solution, wherein the organic acid anhydride reagent is 0.5%-10% of the starch nanoparticles by mass, adjusting the pH to 8-12, placing the mixed solution at 30-55° C. to react for 2-10 h, then adding 0.1-0.5 wt % of an antibacterial agent, and blending, assembling and drying to prepare composite nanoparticles;

(2) according to the proportion of each material added, in parts by weight, mixing 100 parts of bulk starch, 20-60 parts of the composite nanoparticles, 2-5 parts of an etherifying agent, 2-5 parts of a crosslinking agent, and 2-5 parts of a plasticizer, and adjusting to a moisture content of 10-25 wt %; and (3) using a twin-screw extruder as a reactor, setting temperatures of three heating zones of material kneading, melting plasticization, and modification molding at 60-90° C., 90-120° C., and 110-130° C. separately, setting a screw speed as 100-200 r/min, and performing a dry extrusion reaction to obtain the self-reinforced starch-based multifunctional material.

In one embodiment of the disclosure, the starch nanoparticles are derived from natural plant or animal glycogen, synthetic polymer dendritic sugar chains or starch nanocrystals, and have a molecular weight of $10^5$-$10^7$ g/mol and a particle size of 20-100 nm.

In one embodiment of the disclosure, the natural plant or animal glycogen is prepared from natural plant or animal tissue through pulverization, soaking, homogenization, precipitation, and drying to obtain the starch nanoparticles.

In one embodiment of the disclosure, the natural plant or animal glycogen includes one or more of corn glycogen, sorghum glycogen, rice glycogen, barley glycogen, buckwheat glycogen, *Arabidopsis* glycogen, red alga glycogen, blue-green alga glycogen, oyster glycogen, scallop glycogen, Crepidula onyx glycogen and the like, and is prepared by pulverizing, soaking, homogenizing, precipitating and drying feed particles.

In one embodiment of the disclosure, the synthetic polymer dendritic sugar chains include polymer dendritic sugar chains prepared by enzymatic biomimetic synthesis or chemical chain polymerization reaction.

In one embodiment of the disclosure, the enzymatic biomimetic synthesis refers to a process that linear starch short chains undergo multifunctional carbohydrase hydrolysis and glycosidation to catalyze synthesis of polymer dendritic sugar chains in vitro; and the chemical chain polymerization refers to a process that starch sugar chains undergo acid-catalyzed polymerization under high temperature conditions to form polymer dendritic sugar chains.

In one embodiment of the disclosure, the starch nanocrystals are prepared by physical field-assisted concentrated acid hydrolysis of starch, and the method of the physical field-assisted concentrated acid hydrolysis of starch specifically includes: starch is prepared into a starch milk solution, then concentrated sulfuric acid or hydrochloric acid is added, and the mixed solution is placed in a microwave or ultrasonic physical field to react for a period of time to obtain the starch nanocrystals.

In one embodiment of the disclosure, the organic acid anhydride reagent is a compound formed by removing one molecule of water from one or two molecules of organic acid, including, but not limited to, one or more of succinic anhydride, maleic anhydride, acetic anhydride, stearic anhydride, citric anhydride and the like; and the antibacterial agent includes, but is not limited to, one or more of nisin, lysozyme, chitin, ε-polylysine, natamycin, thymol, eugenol, Gemini quaternary ammonium salt and the like.

In one embodiment of the disclosure, the bulk starch includes, but is not limited to, one or more of cereal starch, potato starch, and legume starch, such as corn starch, wheat starch, potato starch, tapioca starch, rice starch, sweet potato starch, mung bean starch and the like, wherein an amylose content in the starch is greater than 35%.

In one embodiment of the disclosure, the etherifying agent is a phase transfer catalyst material synthesized by charge derivatization of starch hydroxyl groups, including, but not limited to, one or more of ethylene oxide, propylene oxide, methyl chloride, 2-chloroethanol, epichlorohydrin, monochloroacetic acid, acrylamide, dimethylsulfuric acid, monohalogenated carboxylic acid, cationic amine reagents and the like; the crosslinking agent is a catalyst material that can form a bridge bond network structure between starch molecular chains, including, but not limited to, one or more of aliphatic dihalogen compounds, tripolyphosphates, sodium trimetaphosphate, citrate, organic mixed acid anhydride, urea, dimethylolurea, dimethylol ethylene urea, acrolein, succinic aldehyde and the like; and the plasticizer is a material that can be added to starch materials to increase the plasticity of polymers, including, but not limited to, one or more of water, glycerin, ethylene glycol, sorbitol, xylitol and the like.

In one embodiment of the disclosure, the aliphatic dihalogen compounds refer to compounds in which specific hydrogen atoms on aliphatic hydrocarbons are replaced with chlorine, fluorine or bromine atoms, and the compounds do not contain a benzene ring or other aromatic rings; and the organic mixed acid anhydride refers to an anhydride formed by dehydration of two or more different organic acids.

The second objective of the disclosure is to provide a self-reinforced starch-based multifunctional material processed by the processing method.

In one embodiment of the disclosure, the self-reinforced starch-based multifunctional material has a tensile strength of greater than 25 MPa, a moisture resistance of less than 6.0 g/(m²×24 h), and a broad-spectrum antibacterial rate of greater than 95%.

The third objective of the disclosure is to provide a film, a packaging product, or a drug carrier and the like containing the self-reinforced starch-based multifunctional material.

The fourth objective of the disclosure is to provide applications of the processing method or the self-reinforced starch-based multifunctional material in the fields of food, textiles, daily chemicals, medicine and the like.

The disclosure has the following advantages:

1. The main raw materials of the disclosure are plant-derived starch such as ordinary cereal starch, potato starch, and legume starch. The raw materials have a wide source and are not restricted by the place of production and seasons.

2. The disclosure is simple and convenient in step, easy in operation, controllable in reaction condition, and relatively low in cost, and the disclosure has basically no pollution to the environment by adoption of a clean and green production technology.

3. The self-reinforced starch-based multifunctional material prepared by the disclosure has good mechanical properties, high barrier properties and high antibacterial properties, can be applied to many fields such as food, textiles, daily chemicals, medicine and the like, and has a broad market prospect.

4. The disclosure utilizes abundant starch resources to develop environment-friendly and recyclable degradable materials, conforms to the strategic industrial development planning of China, and is of great significance for solving oil crisis and plastic pollution, and building a resource-saving and environment-friendly society.

BRIEF DESCRIPTION OF FIGURES

FIG. 1 is an electron micrograph of the self-reinforced starch-based multifunctional material obtained in Example 1.

DETAILED DESCRIPTION

The content of the disclosure will be further clarified below with examples, but the content protected by the disclosure is not limited to the following examples.

Molecular weight determination: The molecular weight is determined by a combined system of high performance liquid phase exclusion chromatography, a multi-angle laser light scattering detector and a differential refractive index detector. The wavelength λ of a He—Ne laser source in the multi-angle laser scattering detector is 632.8 nm. A Shodx OHpak SB-806 chromatographic column is used, a 0.1 mol/L $NaNO_3$ solution is used as a mobile phase, and the flow rate is 0.2 mL/min. The refractive index increment is set to dn/dc=0.138.

Particle size determination: A sample to be tested is prepared into a 0.1% (w/v) solution, and particle size distribution is determined with a Malvern Zetasizer Nano ZS analyzer at 25° C.

Amylose content determination: A reference is made to the method in GB/T 15683-2008 Determination of Amylose Content of Rice for analysis.

Tensile strength determination: A reference is made to the method in the national standard GB/T 1040.2-2006 Determination of Plastic Tensile Properties Part 2: Test Conditions of Molded and Extruded Plastics for analysis.

Moisture resistance determination: A reference is made to the method in GB/T 26253-2010 Determination of Water Vapor Transmission Rate of Plastic Films and Sheets, Infrared Detector Method for analysis.

Determination of broad-spectrum antibacterial rate: Food-borne spoilage bacteria such as *Escherichia coli* (*E. coli*), *Staphylococcus aureus* (*S. aureus*), *Salmonella typhimurium* (*S. typhimurium*), and *Listeria monocytogenes* (*L. monocytogenes*) are streaked on nutrient agar and cultured at 37° C. for 12 h, and then single colonies are selected. Then the single colonies are incubated for 12 h at 37° C. in nutrient broth, plate count is performed, and a certain amount of bacteria is pipetted into 100 mL of nutrient broth (finally $10^7$ CFU/mL). Then an appropriate amount of the self-reinforced starch-based multifunctional material is put for culturing in a constant temperature incubator at 37° C. $OD_{600}$ values of the sample at 0 h, 4 h, 6 h, 8 h, 10 h, 12 h and 24 h are measured, and plate count is performed on the sample cultured for 12 h to determine the antibacterial rate. The determination is performed in triplicate for each group of samples, and the calculation formula is as follows:

$$\text{Antibacterial rate } (\%) = \frac{\text{Bacterial count of control sample} - \text{Recycled Bacterial count}}{\text{Recycled bacterial count of sample}} \times 100.$$

The corn glycogen and the synthetic polymer dendritic sugar chains can be prepared by referring to: Ming Miao, Microbial Starch-Converting Enzymes: Recent Insights and Perspectives, Comprehensive Reviews in Food Science and Food Safety 2018, 17: 1238-1260; The oyster glycogen was purchased from Sigma company.

Example 1

Corn glycogen ($3.1 \times 10^7$ g/mol, particle size 82 nm) and acetic anhydride were mixed in an aqueous solution. The mass fraction of the acetic anhydride relative to the corn glycogen was 1%. The pH was adjusted to 12, the mixed solution was placed at 30° C. to react for 10 h, and 0.1% chitin was added for aggregating and drying to prepare composite nanoparticles. According to the proportion of each material added (weight percentage), 100 parts of corn starch (amylose content 51%), 40 parts of the composite nanoparticles, 2 parts of epichlorohydrin, 5 parts of urea, and 3 parts of glycerin were mixed, and the moisture content was adjusted to 15%. A twin-screw extruder was used as a reactor, the temperatures of three heating zones of material kneading, melting plasticization, and modification molding were set at 60° C., 95° C., and 130° C. separately, the screw speed was set as 150 r/min, and a dry extrusion reaction was performed to obtain a self-reinforced starch-based multifunctional material, the electron micrograph of which is shown in FIG. 1.

The obtained target product self-reinforced starch-based multifunctional material has a tensile strength of 34 MPa, a moisture resistance of 4.6 g/(m²×24 h), and a broad-spectrum antibacterial rate of 98.2%.

Example 2

Oyster glycogen ($7.2 \times 10^6$ g/mol, particle size 67 nm) and citric anhydride were mixed in an aqueous solution. The mass fraction of the citric anhydride relative to the oyster glycogen was 5%. The pH was adjusted to 11, the mixed solution was placed at 50° C. to react for 4 h, and 0.3% nisin was added for aggregating and drying to prepare composite nanoparticles. According to the proportion of each material added (weight percentage), 100 parts of tapioca starch (amylose content 36%), 20 parts of the composite nanoparticles, 5 parts of monochloroacetic acid, 3 parts of citrate, and 4 parts of sorbitol were mixed, and the moisture content was adjusted to 20%. A twin-screw extruder was used as a dry reactor, the temperatures of three heating zones of material kneading, melting plasticization, and modification molding were set at 90° C., 100° C., and 110° C. separately, the screw speed was set as 120 r/min, and extrusion was performed to obtain a self-reinforced starch-based multifunctional material.

The obtained target product self-reinforced starch-based multifunctional material has a tensile strength of 29 MPa, a moisture resistance of 5.1 g/(m²×24 h), and a broad-spectrum antibacterial rate of 99.4%.

Example 3

Synthetic polymer dendritic sugar chains ($8.2 \times 10^5$ g/mol, particle size 44 nm) and stearic anhydride were mixed in an aqueous solution. The mass fraction of the stearic anhydride relative to the synthetic polymer dendritic sugar chains was 8%. The pH was adjusted to 9, the mixed solution was placed at 45° C. to react for 6 h, and 0.5% ε-polylysine was added for aggregating and drying to prepare composite nanoparticles. According to the proportion of each material added (weight percentage), 100 parts of rice starch (amylose content 42%), 60 parts of the composite nanoparticles, 4 parts of methyl chloride, 2 parts of ethylene glycol dimethacrylate, and 4 parts of ethylene glycol were mixed, and the moisture content was adjusted to 18%. A twin-screw extruder was used as a dry reactor, the temperatures of three heating zones of material kneading, melting plasticization, and modification molding were set at 65° C., 90° C., and 120° C. separately, the screw speed was set as 160 r/min, and extrusion was performed to obtain a self-reinforced starch-based multifunctional material.

The obtained target product self-reinforced starch-based multifunctional material has a tensile strength of 32 MPa, a moisture resistance of 4.1 g/(m²×24 h), and a broad-spectrum antibacterial rate of 99.0%.

When the starch nanoparticles, organic acid anhydrides, antibacterial agents, bulk starch, etherifying agents, cross-linking agents, plasticizers and the like in the above examples are replaced with other materials described in the disclosure, self-reinforced starch-based multifunctional materials can also be prepared and have a tensile strength of greater than 25 MPa, a moisture resistance of less than 6.0 g/(m²×24 h), and a broad-spectrum bacteriostatic rate of greater than 95%.

Comparative Example 1

Referring to Example 1, when composite nanoparticles were not prepared, according to the proportion of each material added (weight percentage), 100 parts of corn starch (amylose content 51%), 2 parts of epichlorohydrin, 5 parts of urea, 3 parts of glycerin and 4 parts of bacteriostatic chitin were mixed, and the moisture content was adjusted to 15%. A twin-screw extruder was used as a reactor, the temperatures of three heating zones of material kneading, melting plasticization, and modification molding were set at 60° C., 95° C. and 130° C. separately, the screw speed was set as 150 r/min, and a dry extrusion reaction was performed to obtain a material.

After testing, the material has a tensile strength of 21 MPa, a moisture resistance of 6.7 g/(m²×24 h), and a broad-spectrum antibacterial rate of 57%.

Comparative Example 2

Referring to Example 1, when no chitin was added to the composite nanoparticles, according to the proportion of each material added (weight percentage), 100 parts of corn starch (amylose content 51%), 40 parts of the composite nanoparticles, 2 parts of epichlorohydrin, 5 parts of urea and 3 parts of glycerin were mixed, and the moisture content was adjusted to 15%. A twin-screw extruder was used as a reactor, the temperatures of three heating zones of material kneading, melting plasticization, and modification molding were set at 60° C., 95° C. and 130° C. separately, the screw speed was set as 150 r/min, and a dry extrusion reaction was performed to obtain a material.

After testing, the material has a tensile strength of 27 MPa, a moisture resistance of 5.9 g/(m²×24 h), and a broad-spectrum antibacterial rate of 0%.

Comparative Example 3

Referring to Example 1, the mass fraction of the acetic anhydride added in the preparation of the composite nanoparticles was replaced with 0%, 0.2%, and 30%, respectively, to obtain the corresponding starch-based material properties. The properties of the products obtained are shown in Table 1.

TABLE 1

Properties of products obtained with different amounts of organic acid anhydride reagent

| Mass fraction of organic acid anhydride reagent | Tensile strength MPa | Moisture resistance g/(m² × 24 h) | Broad-spectrum antibacterial rate % |
|---|---|---|---|
| 0% | 23 | 6.3 | 70 |
| 0.2% | 26 | 6.6 | 87 |
| 30% | 26 | 6.1 | 91 |

Comparative Example 4

Referring to Example 1, the mass fraction of moisture in the dry extrusion reaction was controlled to 0%, 5% and 40%, respectively, to obtain the corresponding starch-based material properties. The properties of the products obtained are shown in Table 2.

TABLE 2

Properties of the products prepared under different mass fractions of moisture in the dry extrusion reaction

| Mass fraction of moisture | Tensile strength MPa | Moisture resistance g/(m² × 24 h) | Broad-spectrum antibacterial rate % |
|---|---|---|---|
| 0% | 22 | 5.9 | 96 |
| 5% | 24 | 5.6 | 95 |
| 40% | 17 | 6.6 | 85 |

Comparative Example 5

Referring to Example 1, when no epichlorohydrin was added, a material was obtained by dry extrusion reaction.

After testing the properties of the starch-based material, the tensile strength is 16 MPa, the moisture resistance is 6.3 g/(m²×24 h), and the broad-spectrum antibacterial rate is 96%.

Comparative Example 6

Referring to Example 1, when no urea was added, a material was obtained by dry extrusion reaction.

After testing the properties of the starch-based material, the tensile strength is 23 MPa, the moisture resistance is 6.1 g/(m²×24 h), and the broad-spectrum antibacterial rate is 97%.

Although the disclosure has been disclosed as above in preferred examples, it is not intended to limit the disclosure. Those skilled in the art can make various changes and modifications without departing from the spirit and scope of the disclosure. Therefore, the protection scope of the disclosure should be defined by the claims.

What is claimed is:

1. A method of manufacturing a self-reinforced starch-based multifunctional material, which comprises:
    (a) mixing starch nanoparticles, each having a particle size of 20 nm to 100 nm, and an organic acid anhydride reagent in an aqueous solution, wherein the organic acid anhydride reagent is 0.5% to 10% of the starch nanoparticles by mass, wherein the starch nanoparticles are derived from natural plant glycogen, animal glycogen, synthetic polymer dendritic sugar chains, or starch nanocrystals, each having a molecular weight of $10^5$ to $10^7$ g/mol,
    (b) adjusting pH to 8 to 12, thereby forming a mixed solution,
    (c) reacting the mixed solution at 30° C. to 55° C. for 2 hours to 10 hours, thereby forming a reacted solution,
    (d) blending 0.1 wt % to 0.5 wt % of an antibacterial agent into the reacted solution, thereby forming a blend,
    (e) drying the blend to thereby prepare composite nanoparticles,
    (f) preparing a composition according to the proportion of each material added, in parts by weight, by mixing 100 parts of bulk starch, 20 parts to 60 parts of the composite nanoparticles, 2 parts to 5 parts of an etherifying agent, 2 parts to 5 parts of a crosslinking agent, and 2 parts to 5 parts of a plasticizer,
    (g) adjusting the composition formed in step (g) of step (f) to a moisture content of 10 wt % to 25 wt %; and
    (h) feeding the composition into a twin-screw extruder, wherein three heating zones of the twin-screw extruder of material kneading, melting plasticization, and modification molding are 60° C. to 90° C., 90° C. to 120° C., and 110° C. to 130° C., respectively, and wherein the twin-screw extruder has a screw speed of 100 r/min to 200 r/min, thereby obtaining the self-reinforced starch-based multifunctional material.

2. The method according to claim 1, wherein:
    the organic acid anhydride reagent comprises one or more of: succinic anhydride, maleic anhydride, acetic anhydride, stearic anhydride and citric anhydride; and
    the antibacterial agent comprises one or more of nisin, lysozyme, chitin, ε-polylysine, natamycin, thymol, eugenol, and Gemini quaternary ammonium salt.

3. The method according to claim 1, wherein the bulk starch comprises cereal starch, potato starch, or legume starch.

4. The method according to claim 1, wherein the bulk starch comprises one or more of corn starch, wheat starch, potato starch, tapioca starch, rice starch, sweet potato starch, and mung bean starch.

5. The method according to claim 1, wherein:
    the etherifying agent comprises one or more of ethylene oxide, propylene oxide, methyl chloride, 2-chloroethanol, epichlorohydrin, acrylamide, dimethylsulfuric acid, monohalogenated carboxylic acid, and cationic amine reagents;
    the cross-linking agent comprises one or more of aliphatic dihalogen compounds, tripolyphosphates, sodium trimetaphosphate, citrate, organic mixed acid anhydride, urea, dimethylolurea, dimethylol ethylene urea, acrolein, and succinic aldehyde; and
    the plasticizer comprises one or more of water, glycerin, ethylene glycol, sorbitol, and xylitol.

6. The method according to claim 3, wherein:
    the etherifying agent comprises one or more of ethylene oxide, propylene oxide, methyl chloride, 2-chloroethanol, epichlorohydrin, acrylamide, dimethylsulfuric acid, monohalogenated carboxylic acid, and cationic amine reagents;
    the cross-linking agent comprises one or more of aliphatic dihalogen compounds, tripolyphosphates, sodium trimetaphosphate, citrate, organic mixed acid anhydride, urea, dimethylolurea, dimethylol ethylene urea, acrolein and succinic aldehyde; and the plasticizer comprises one or more of water, glycerin, ethylene glycol, sorbitol, and xylitol.

7. The method according to claim 5, wherein the monohalogenated carboxylic acid is monochloroacetic acid.

* * * * *